US011786143B2

(12) United States Patent
Muessig et al.

(10) Patent No.: US 11,786,143 B2
(45) Date of Patent: Oct. 17, 2023

(54) ACTIVE MEDICAL DEVICE CAPABLE OF IDENTIFYING COUGHING

(71) Applicant: BIOTRONIK SE & Co. KG, Berlin (DE)

(72) Inventors: Dirk Muessig, West Linn, OR (US); Ravi Kiran Kondama Reddy, Portland, OR (US); R. Hollis Whittington, Portland, OR (US); Thomas Doerr, Berlin (DE); Shayan Guhaniyogi, Portland, OR (US)

(73) Assignee: BIOTRONIK SE & Co. KG, Berlin (DE)

( * ) Notice: Subject to any disclaimer, the term of this patent is extended or adjusted under 35 U.S.C. 154(b) by 150 days.

(21) Appl. No.: 17/329,861

(22) Filed: May 25, 2021

(65) Prior Publication Data

US 2021/0369139 A1 Dec. 2, 2021

Related U.S. Application Data

(60) Provisional application No. 63/029,722, filed on May 26, 2020.

(30) Foreign Application Priority Data

Sep. 15, 2020 (EP) ..................... 20196096

(51) Int. Cl.
*A61B 5/08* (2006.01)
*A61B 5/0538* (2021.01)
*A61B 5/00* (2006.01)

(52) U.S. Cl.
CPC .......... *A61B 5/0823* (2013.01); *A61B 5/0538* (2013.01); *A61B 5/686* (2013.01);
(Continued)

(58) Field of Classification Search
CPC combination set(s) only.
See application file for complete search history.

(56) References Cited

U.S. PATENT DOCUMENTS

| 2004/0133079 | A1 | 7/2004 | Mazar et al. |
| 2009/0203972 | A1* | 8/2009 | Heneghan ............. G16H 40/63 600/301 |

(Continued)

OTHER PUBLICATIONS

Godfrey, A., Bourke, A. K., Ólaighin, G. M., van de Ven, P., Nelson, J. (2011). Activity classification using a single chest mounted tri-axial accelerometer. Medical Engineering Physics, 33(9), 1127-1135. https://doi.org/10.1016/j.medengphy.2011.05.002 (Year: 2011).*

(Continued)

*Primary Examiner* — Eric F Winakur
*Assistant Examiner* — Elina Sohyun Ahn
(74) *Attorney, Agent, or Firm* — Buchanan Ingersoll & Rooney PC

(57) ABSTRACT

An active medical device, comprising a processor, a memory unit, and at least one of an accelerometer and a detection unit configured to detect a body impedance. During operation, the active medical device carries out the following steps: a) measuring a body impedance of a patient with the detection unit during a first period of time to obtain time-dependent impedance data and calculating a power spectral density of the impedance data; b) alternatively or additionally to step a), measuring an acceleration of a body of the patient with the accelerometer during the first period of time to obtain time-dependent acceleration data and calculating a power spectral density of the acceleration data; c) identifying coughing of the patient on the basis of the calculated power spectral density if at least 1% of all values of the power spectral density have a frequency of at least 1 Hz.

15 Claims, 7 Drawing Sheets

(52) U.S. Cl.
CPC ............. *A61B 2560/0219* (2013.01); *A61B 2562/0219* (2013.01)

(56) References Cited

U.S. PATENT DOCUMENTS

| | | |
|---|---|---|
| 2011/0125044 A1 | 5/2011 | Rhee et al. |
| 2012/0302898 A1* | 11/2012 | Zhang ................. A61B 5/0823 |
| | | 607/18 |
| 2012/0302921 A1* | 11/2012 | Gavriely ............... A61B 5/113 |
| | | 600/586 |
| 2019/0069840 A1 | 3/2019 | Young et al. |
| 2020/0038660 A1 | 2/2020 | Torgerson |
| 2020/0069281 A1 | 3/2020 | Chan et al. |
| 2020/0359934 A1* | 11/2020 | Banet .................... A61B 5/113 |
| 2021/0106253 A1* | 4/2021 | Gunderson ............ A61B 5/352 |
| 2021/0153773 A1* | 5/2021 | Wei ...................... A61B 5/6823 |
| 2021/0219925 A1* | 7/2021 | Au ....................... A61B 5/1135 |

OTHER PUBLICATIONS

Adler, A., Guardo, R., Berthiaume, Y. (1996). Impedance imaging of lung ventilation: Do we need to account for chest expansion? Proceedings of 16th Annual International Conference of the IEEE Engineering in Medicine and Biology Society. https://doi.org/10.1109/iembs.1994.411917 (Year: 1996).*

European Search Report and Annex to the European Search Report on European Patent Application No. EP 20 19 6096.0, dated Mar. 10, 2021 (11 pages).

* cited by examiner

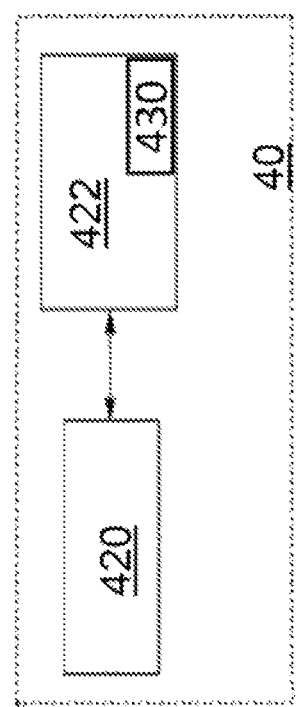

ACTIVE MEDICAL DEVICE CAPABLE OF IDENTIFYING COUGHING

CROSS-REFERENCE TO RELATED APPLICATIONS

This patent application claims the benefit of and priority to U.S. Provisional Patent Application No. 63/029,722, filed May 26, 2020. which is hereby incorporated by reference in its entirety.

TECHNICAL FIELD

The present invention relates to an active medical device according to the preamble of claim 1, to an arrangement comprising such an active medical device according to the preamble of claim 9, and to a computer program product according to the preamble of claim 12.

BACKGROUND

Coughing is early indicator for infection, e.g., for a viral infection such as influenza or COVID-19.

U.S. Publication No, 2004/0133079 describes the general possibility to use transthoracic impedance variation patterns or acceleration data for identifying an occurrence of a disease like asthma or COPD.

U.S. Publication No, 2020/0038660 discloses detecting of coughing or other body reactions as side effect of an action potential evoked by a cardiac implant. Furthermore, this patent application discloses the possibility to postpone or adjust the application of action potentials in reaction to detected coughing.

However, it turned out that simply relying on bare data provided by acceleration sensors or transthoracic impedance sensors does not always allow detection of coughing with a sufficient sensitivity and/or specificity.

The present disclosure is directed toward overcoming one or more of the above-mentioned problems, though not necessarily limited to embodiments that do.

SUMMARY

It is an object of the present invention to provide a possibility to automatically detect coughing of a patient with a higher reliability than according to prior art techniques.

At least this object is achieved with an active medical device having the claim elements of claim 1.

An "active medical device" is typically defined to be any medical device relying for its functioning on a source of electrical energy or any source of power other than that directly generated by the human body or gravity.

The presently claimed active medical device comprises a processor, a memory unit, and at least one of an accelerometer (i.e., a device for detecting an acceleration) and a detection unit configured to detect a body impedance.

According to aspect of the presently claimed invention, the memory unit comprises a computer-readable program that causes the processor to perform the following steps when executed on the processor:
a) measuring a body impedance of a patient with the detection unit during a first period of time to obtain time-dependent impedance data and calculating a power spectral density of the impedance data;
b) alternatively or additionally to step a), measuring an acceleration of a body of the patient with the accelerometer during the first period of time to obtain time-dependent acceleration data and calculating a power spectral density of the acceleration data;
c) identifying, coughing of the patient on the basis of the calculated power spectral density, if at least 1% of all values of the power spectral density have a frequency of at least 1 Hz;
wherein the computer-readable program causes the processor to identify coughing of the patient on the basis of the calculated power spectral density if at least 60% of the power in the power spectral density is contained in the frequency band of 1 to 8 Hz.

Additional features, aspects, objects, advantages, and possible applications of the present disclosure will become apparent from a study of the exemplary embodiments and examples described below, in combination with the Figures and the appended claims.

BRIEF DESCRIPTION OF THE DRAWINGS

Further details of aspects of the present invention will be explained in the following with respect to exemplary embodiments and accompanying Figures. In the Figures:

FIG. 3 shows a schematic view of an evaluation unit in accordance with the present invention;

DETAILED DESCRIPTION

Figure 1:
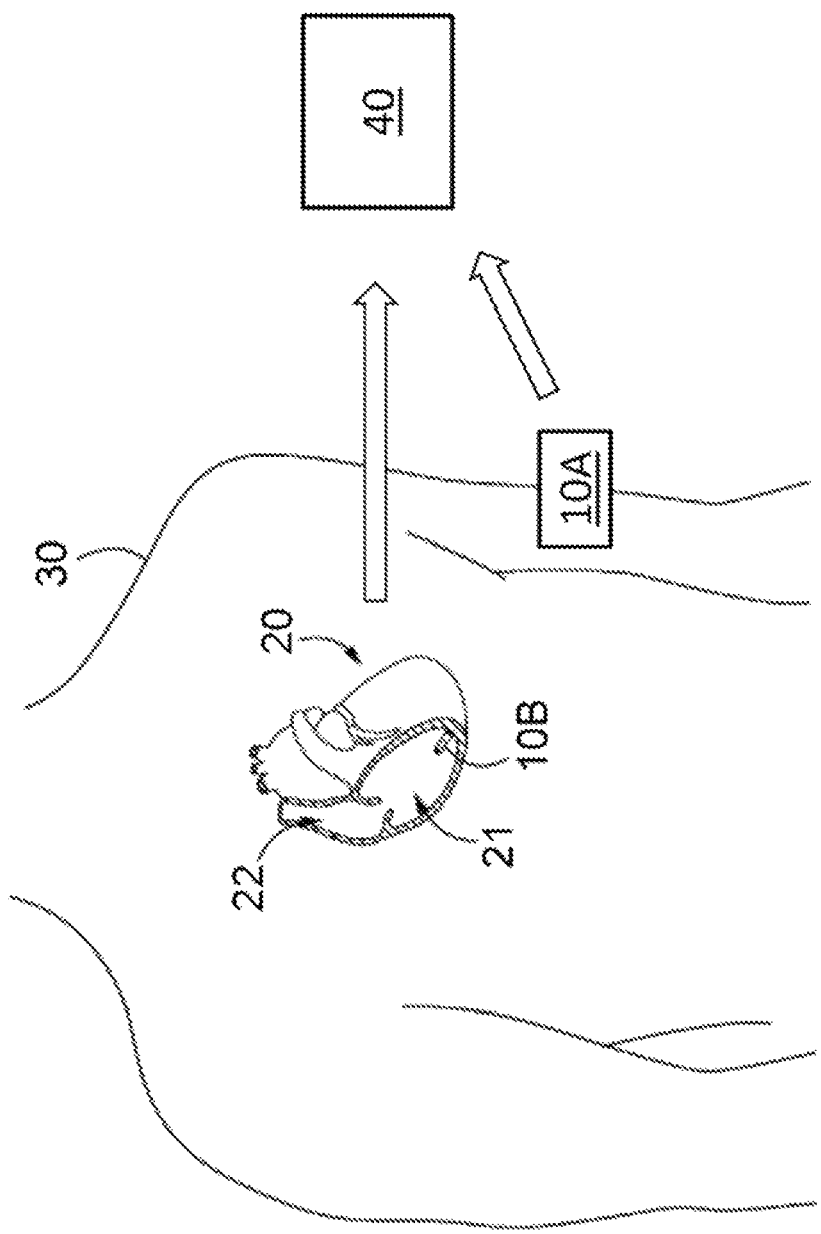
FIG. 1 shows an active medical device in accordance with the present invention implanted in a patient and worn by a patient and in communication with an external evaluation unit.

FIG. 1 illustrates the active medical device 10A which is wearable by a patient 30, and the active medical device 10B implanted in a human patient 30 (although it could also be implanted in an animal) and attached to the heart 20. The heart 20 includes a right ventricle 21 and a right atrium 22 (and corresponding left ventricle and atrium-now shown). The active medical device 10A, 10B communicates with an evaluation unit 40 positioned outside the patient's body.

Figure 2:
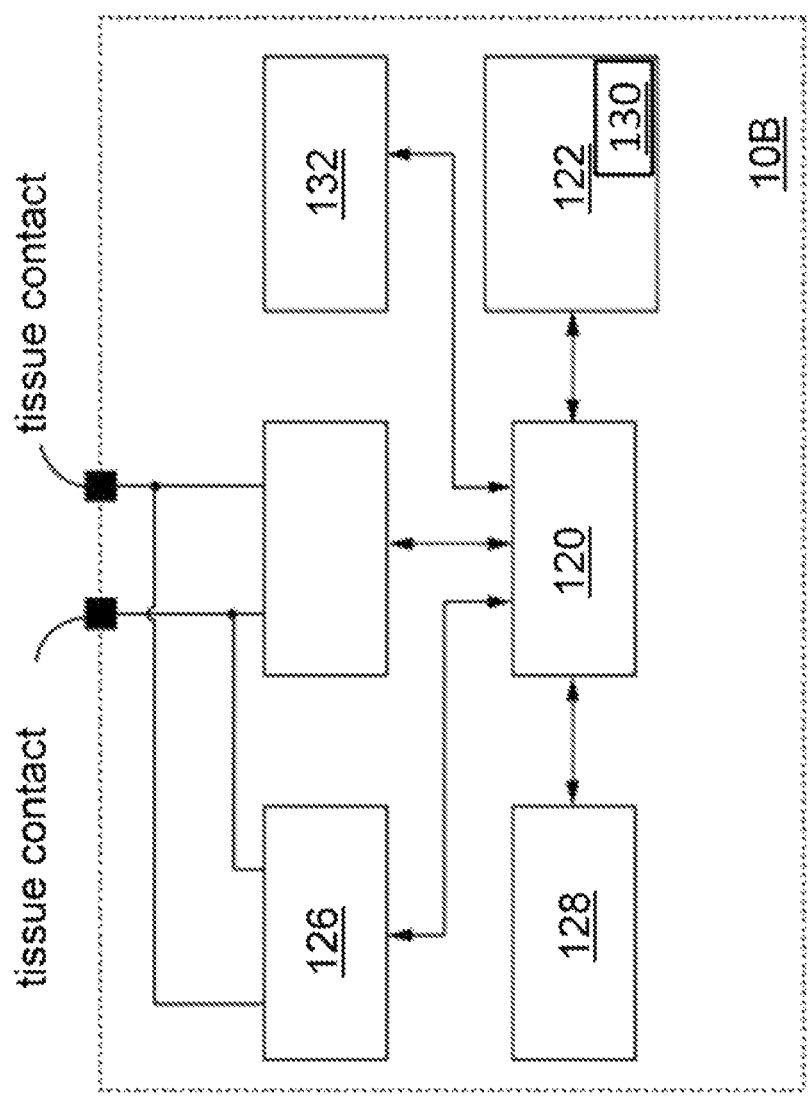
FIG. 2 shows a schematic view of an active medical device ire accordance with the present invention.

FIG. 2 illustrates the active medical device 10B attached to the heart 20 that serves for monitoring a human or animal heart 20. The active medical device 10B is connected to the heart 20 at tissue contacts, and comprises a processor 120, a memory unit 122, a detection unit 126, a data communication unit 128, and an accelerometer 132. The detection unit 126 serves for detecting an electrical signal of the heart 20 and measuring a body impedance. The accelerometer 132 serves for measuring an acceleration of the body of the patient 30.

According to the presently claimed invention, the memory unit 122 comprises a computer-readable program 130 that causes the processor 120 to perform the steps explained in the following when executed on the processor 120.

In a first step, a body impedance of a patient is measured with the detection unit 126 during a first period of time. As a result, time-dependent impedance data is obtained. This time-dependent impedance data is used to calculate to power spectral density of the impedance data. The power spectral density (PSD) describes how the power of a signal or a time series is distributed over frequency. The power spectral density is sometimes also referred to as power spectrum.

Alternatively or additionally to the precedingly explained step, an acceleration of the body of the patient is measured with the accelerometer 132 during the first period of time. As a result, time-dependent acceleration data is obtained. This acceleration data is then used for calculating a power spectral density of the acceleration data. Thus, either a single power spectral density or two different power spectral densities are calculated.

Subsequently, a coughing (or a coughing event) of the patient is identified on the basis of the calculated power spectral density. To be more precise, a coughing of the patient is identified if at least 1%, in particular at least 2%, in particular at least 3%, in particular at least 4%, in particular at least 5%, in particular at least 6%, in particular at least 7%, in particular at least 8%, in particular at least 9%, in particular at least 10%, in particular at least 15%, in particular at least 20%, in particular at least 25%, in particular at least 30%, in particular at least 40%, in particular at least 50% of all values of the power spectral density have a frequency of at least 1 Hz, in particular of at least 1.5 Hz, in particular at least 2 Hz, in particular at least 2.5 Hz, in particular at least 3 Hz.

According to a particular embodiment, coughing of the patient is identified if die relative power in a frequency band above 1 Hz is at least 60% of the total power in the PSD.

In case of natural respiration, typically more than 80% of the total power in the power spectral density of acceleration data or impedance data of a patient lies within frequencies less than 1 Hz. Therewith, the power spectral density constitutes a powerful tool in distinguishing natural respiration from coughing events. In contrast, by simply evaluating the bare acceleration or the bare impedance data, it is often difficult to distinguish a coughing event from the natural respiration since the acceleration changes or impedance changes are rather moderate. Furthermore, it is necessary to define a distinct threshold for acceleration change and a distinct threshold for impedance change to make a distinction between natural respiration and coughing. In contrast, by using the power spectral density, the same threshold values can be used for the obtained impedance data and the obtained acceleration data since the frequency domain of this data is evaluated. This facilitates data evaluation, reduces the risk of erroneously incorrect assigned or interpreted data and makes an automatic coughing detection much more reliable than this was possible by applying prior art techniques. The power spectral density can thus be seen as a universal tool making it possible to evaluate different kinds of data (namely, acceleration data and impedance data) in the same way for an automatic coughing detection.

In an embodiment, the power spectral density at a frequency k for a discrete-time acceleration or impedance signal x(n) is calculated according to the following equation:

$$P(k) = \frac{|X(k)|^2}{f_s N}$$

where X(k) is the discrete fourier transform (i)FT of the signal x(n), fs is the sampling frequency of the signal x(n), and N is the number of samples in x(n). Given a frequency range of interest 0 Hz to fb Hz (where fb<fs/2), the relative power in a subset of that band [fl Hz to fh Hz] is then given by:

$$\frac{\sum_{k=fl}^{fh} P(k)}{\sum_{k=0}^{fb} P(k)}$$

In an embodiment, the relative power in the subset frequency band above 1 Hz lies in a range between fl=1 Hz and fh=8 Hz, in particular between 1.5 Hz and 12.5 Hz, in particular between 2 Hz and 10 Hz, in particular between 2.5 Hz and 9 Hz, in particular between 3 Hz and 8 Hz (including the upper and lower limit in each case). Thus coughing is identified if:

$$\frac{\sum_{k=1\,Hz}^{8\,Hz} P(k)}{\sum_{k=0\,Hz}^{8\,Hz} P(k)} > 0.6$$

In an embodiment, the first period of time is a time period lying in a range of from 10 seconds to 1 day, in particular from 15 seconds to 23 hours, in particular from 20 seconds to 22 hours, in particular from 30 seconds to 21 hours, in particular from 45 seconds to 20 hours, in particular from 1 minute to 19 hours, in particular from 2 minutes to 18 hours, in particular from 3 minutes to 17 hours, in particular from 4 minutes to 16 hours, in particular from 5 minutes to 15 hours, in particular from 6 minutes to 14 hours, in particular from 10 minutes to 13 hours, in particular from 15 minutes to 12 hours, in particular from 30 minutes to 11 hours, in particular from 45 minutes to 10 hours, in its particular from 1 hour to 9 hours, in particular from 2 hours to 8 hours, in particular from 3 hours to 7 hours, in particular from 4 hours to 6 hours.

In an embodiment, the active medical device 10A is a wearable device. Thus, in this embodiment, the active medical device 10A can be worn by patient on the body. This makes an application of the active medical device 10A particularly simple. An appropriate wearable device is a wearable device in form of a wristband or in form of a chest band. In an embodiment, the active medical device 10A is realized in form of a smartwatch.

In an embodiment, the active medical device 10B is an active implantable medical device. An "active implantable medical device" is typically defined to be any active medical device 10B which is intended to be totally or partially introduced, surgically or medically, into the human body or by medical intervention into a natural orifice, and which is intended to remain after the procedure.

Further details on active implantable medical implants can be found, e.g., in the consolidated text of the Council Directive 90/385/EEC of 20 Jun. 1990 on the approximation of the laws of the Member States relating to active implantable medical devices with subsequent amendments in the version published on 11 Oct. 2007. The consolidated text of this Council Directive is freely accessible.

In an embodiment, the active implantable medical device 10B is an implantable pulse generator (IPG), an implantable cardioverter-defibrillator (ICD), a device for cardiac resynchronization therapy (CRT), or an implantable cardiac monitor. An appropriate cardiac monitor is a loop recorder.

The detection unit 126 configured to detect the body impedance typically comprises at least two electrodes between which an impedance is measured. In sonic instances, a housing of the active medical device 10A, 10B can be used as one of these electrodes. In an embodiment, the detection unit 126 is configured to detect a transthoracic body impedance. The transthoracic impedance is particularly responsive to sudden movements of the thorax of the patient, such as in case of a coughing event.

In an embodiment, the computer-readable program 130 causes the processor 120 to additionally detect a position of the patient relative to a ground and/or an activity status of the patient. For this purpose, the accelerometer 132 is used. In an embodiment, the accelerometer 132 is a 3-axis accelerometer. Such a 3-axis accelerometer makes it particularly easy to measure patient activity and/or patient position.

In an embodiment, the computer-readable program 130 causes the processor 120 to indicate a validity (i.e., a reliability) of the identification of coughing on the basis of the detected position and/or the detected activity status of the patient. An appropriate activity status is "active" (as in case of walking, running or moving otherwise), "non-active" (as in case of resting or sitting calmly) or "in between" (as in case of an activity status lying between "active" and "non-active"). To give an example, if the position of the patient was identified to be supine and the activity status of the patient was identified to be "non-active", then signals in the power spectral density having a frequency of more than 1 Hz are particularly specific for a coughing event since no other physiologic movements of the thorax of the patient with such a frequency are to be expected in such a position and such an activity status. Thus, in such a case, the validity value assigned to the identified coughing event is high to indicate a high reliability of the identification of the coughing.

In an embodiment, the computer-readable program 130 causes the processor 120 to identify an amount (e.g., a number) of identified coughing events of the patient. This amount of identified coughing events can be stored in the active medical device 10A, 10B and can be reported immediately or with a temporal postponement to an external server such as a cloud computing device. The amount of identified coughing, events is, in an embodiment, referred to a specific timeframe, such as the first time period. To give an example, the amount of identified coughing events per day can be stored within the active medical device 10A, 10B or can be transferred to an external computing device so that medical staff such as a physician can further review and evaluate the data afterwards.

In an embodiment, the computer-readable program 130 causes the processor 120 to create an alert if the amount of identified coughing events of the patient, in particular of identified coughing events per time period, exceeds a predetermined threshold. Such an alert can be used to indicate that an infection of the patient is likely. This can be used as an indication that the patient is suffering from a disease such as a viral disease like influenza or COVID-19. A physician can then decide on necessary clinical or pandemic measures, in particular after having further examined the patient and after having made a diagnosis of a specific disease or a prognosis on the likelihood that the patient suffers from a specific disease. Alternatively, the alert on a suspected coughing-related infection (e.g., a potential influenza infection or a potential COVID-19 infection) can be automatically processed and communicated to the patient.

In an embodiment, the threshold lies in a range of from 1 cough per minute to 5 coughs per 10 seconds, in particular from 2 coughs per minute to 4 coughs per 10 seconds, in particular from 3 coughs per minute to 3 coughs per 10 seconds, in particular from 4 coughs per minute to 2 coughs, per 10 seconds, in particular from 5 coughs per minute to 1 cough per 10 seconds.

In an aspect, the present invention relates to an arrangement comprising an active medical device 10A, 10B, in particular an active medical device 10A, 10B according to the preceding explanations, and an evaluation unit 40 separate from the active medical device 10A, 10B. In this context, the active medical device 10A, 10B comprises a first processor 120, a first memory unit 122, at least one of an accelerometer 132 and a detection unit 126 configured to detect body impedance, and a data communication unit 128.

The first memory unit 122 comprises a first computer-readable program 130 that causes the first processor 120 to perform the steps explained in the following when executed on the first processor 120.

First, a body impedance of a patient is measured with the detecting unit during the first period of time. In doing so, time-dependent impedance data is obtained.

Alternatively or additionally to the step of measuring a body impedance, an acceleration of the body of the patient is measured during the first period of time to obtain time-dependent acceleration data.

The impedance data and/or the acceleration data is then transmitted via the data communication unit 128 to the evaluation unit 40 located outside a body of the patient.

As shown in FIG. 3, the evaluation unit 40 comprises a second processor 420 and a second memory unit 422. In this context, the second memory unit 422 comprises a second computer-readable program 430 that causes the second processor 420 to perform the steps explained the following when executed on the second processor 420.

First, the transmitted impedance data and/or the transmitted acceleration data (depending on which kind of data has been transmitted to the evaluation unit 40) is stored in the second memory unit 422.

Afterwards, a power spectral density of the impedance data and/or a power spectral density of the acceleration data (depending on which kind of data has been transmitted to the evaluation unit 40 and stored in the second memory unit 422) is calculated.

Afterwards, a coughing of the patient is automatically identified on the basis of the calculated power spectral density. In this context, an event is considered to be coughing if at least 60% of the power in the power spectral density is contained in the frequency band of 1 to 8 Hz.

All embodiments explained above with respect to the memory unit and/or the processor can be transferred to the first memory unit 122 or the first processor 120, respectively, and/or the second memory unit 422 or the second processor 420, respectively, of the described arrangement.

In an embodiment, the data communication unit 128 serves for transferring data to the evaluation unit 40 in a wireless manner. All standard data transmission protocols or specifications are appropriate for such a wireless data communication. Examples of standard data transmission protocols or specifications are the Medical Device Radiocommunications Service (MICS), the Bluetooth Low Energy (BLE) protocol and the Zigbee specification.

In an aspect, the present invention relates to a computer program product comprising computer-readable code that causes a processor 120 to perform the steps explained in the following when executed on the processor 120.

In a first step, a body impedance of a patient is measured with a detection unit 126 of an active medical device 10A, 10B during a first period of time. As a result, time-dependent impedance data is obtained. This time-dependent impedance data is used to calculate a power spectral density of the impedance data.

Alternatively or additionally to the precedingly explained step, an acceleration of the body of the patient is measured with an accelerometer 132 of the active medical device 10A, 10B during the first period of time. As a result, time-dependent acceleration data is obtained. This acceleration data is then used for calculating a power spectral density of the acceleration data. Thus, either a single power spectral density or two different power spectral densities are calculated.

Subsequently, a coughing (or a coughing event) of the patient is identified on the basis of the calculated power spectral density. To be more precise, a coughing of the patient is identified if at least 60% of the power in the power spectral density is contained in the frequency band of 1 to 8 Hz.

In an aspect, the present invention relates to a method for automatically detecting coughing of a patient. Thereby, the method comprises the steps explained in the following.

In a first step, a body impedance of a patient is measured with a detection unit 126 of an active medical device 10A, 10B during a first period of time. As a result, time-dependent impedance data is obtained. This time-dependent impedance data is used to calculate a power spectral density of the impedance data.

Alternatively or additionally to the precedingly explained step, an acceleration of the body of the patient is measured with an accelerometer 132 of the active medical device 10A, 10B during the first period of time. As a result, time-dependent acceleration data is obtained. This acceleration data is then used for calculating a power spectral density of the acceleration data. Thus, either a single power spectral density or two different power spectral densities are calculated.

Subsequently, a coughing (or a coughing event) of the patient is identified on the basis of the calculated power spectral density. To be more precise, a coughing of the patient is identified if at least 60% of the power in the power spectral density is contained in the frequency band of 1 to 8 Hz, In an embodiment, the method comprises the step of indicating to the patient or to medical staff an increased risk of an infection, in particular of a viral infection such as an influenza or COVID-19 infection if an amount of identified coughing events, in particular an amount of identified coughing events per time period, of the patient exceeds a predetermined threshold.

All embodiments of the described active medical device 10A, 10B can be combined in any desired way and can be transferred either individually or in any arbitrary combination to the described arrangement, the described computer program product and the described method. Furthermore, all embodiments of the described arrangement can be combined in any desired way and can be transferred either individually or in any arbitrary combination to the active medical device 10A, 10B, to the computer program product and to the described method. Likewise, all embodiments of the computer program product can be combined in any desired way and can be transferred either individually or in any arbitrary combination to the active medical device 10A, 10B, to the arrangement and to the its described method. Lastly, all embodiments of the described method can be combined in any desired way and can be transferred either individually or in any arbitrary combination to the active medical device 10A, 10B, to the arrangement and to the computer program product.

Figure 4A:
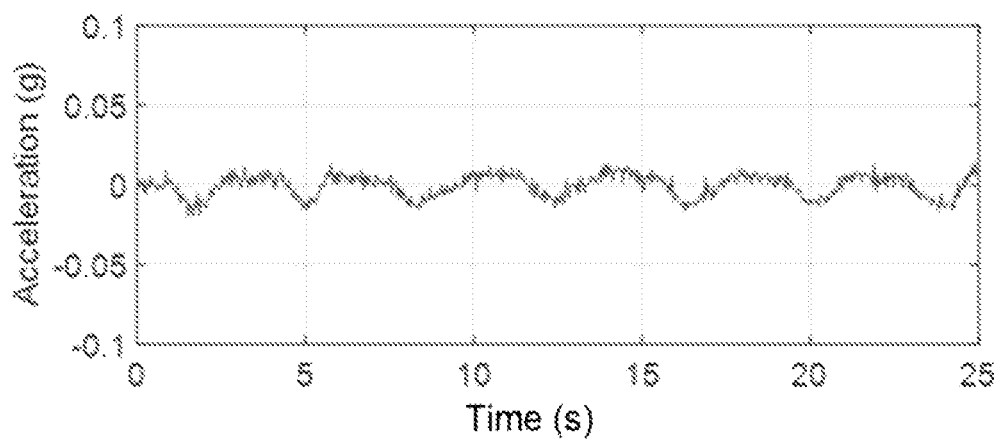
FIG. 4A shows time-dependent acceleration data of a patient having nature respiration.
Figure 4B:
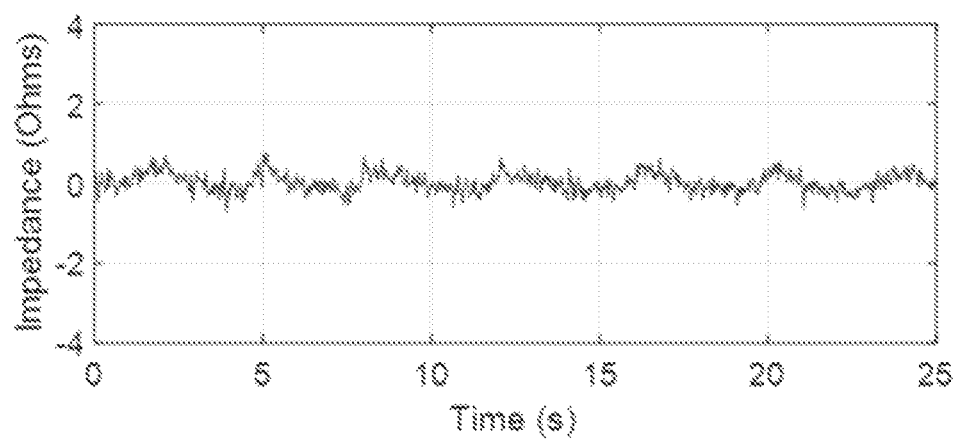
FIG. 4B shows time-dependent impedance signals of a patient having natural respiration.

FIG. 4A shows an acceleration measured by an active medical device 10A, 10B over time during a patient's natural respiration. A loss amplitude, low-frequency periodic waveform can be observed. A similar signal yet on a different scale and somewhat less pronounced can be observed in case of a transthoracic impedance measured by an active medical device 10A, 10B over time (cf. FIG. 4B).

Figure 5A:
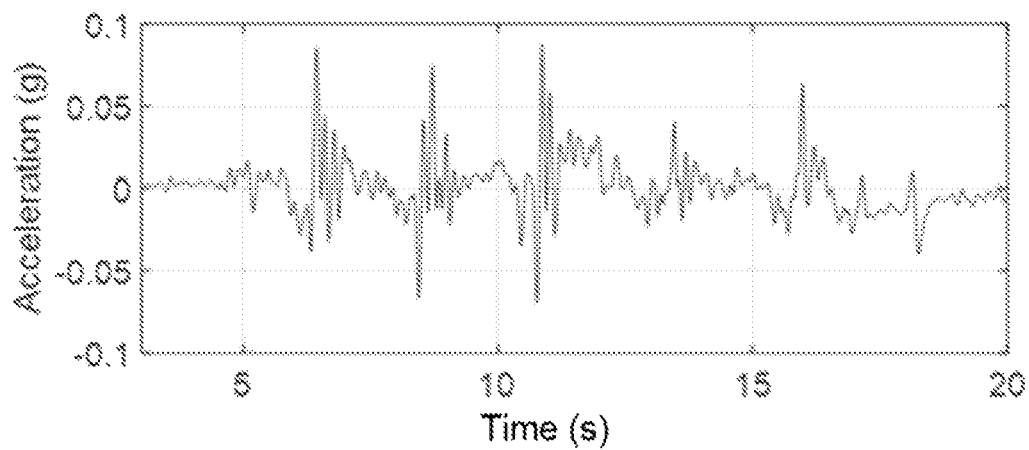
FIG. 5A shows time-dependent acceleration data of a coughing patient.
Figure 5B:
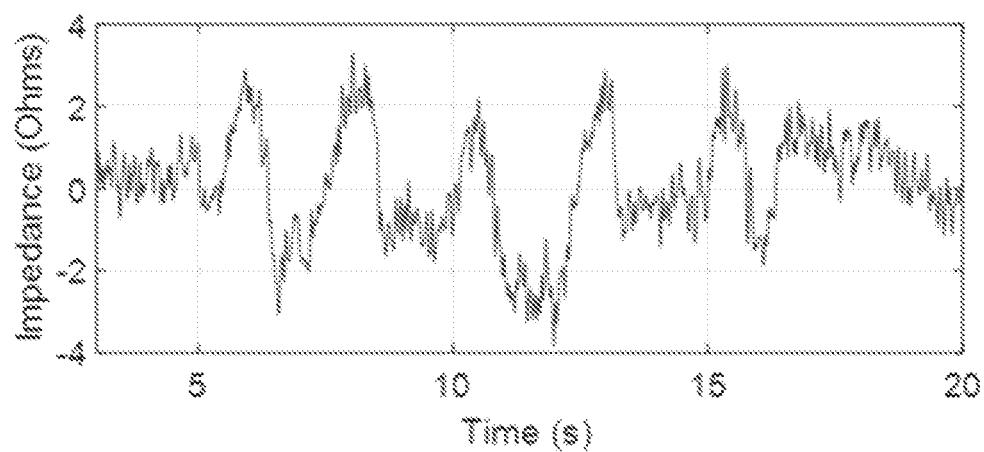
FIG. 5B shows time-dependent impedance signals of a coughing patient

In contrast, coughing of the patient leads to more or less regularly distributed spikes both in the acceleration signal (FIG. 5A) and in the impedance signal (FIG. 5B). Both the acceleration signal of FIG. 5A and the impedance signal of FIG. 5B relates to five coughs of the patient. It can be easily seen from FIGS. 5A and 5B that not all of these coughs are equally pronounced. Thus, while individual spikes might be correctly assigned to coughs, this is not true with respect to other spikes, e.g., the signal at approximately 13 seconds in FIG. 5A. Thus, the "disturbances" observed in the acceleration signal and the impedance signal are difficult to evaluate and to be correctly assigned to coughing events.

Figure 6A:
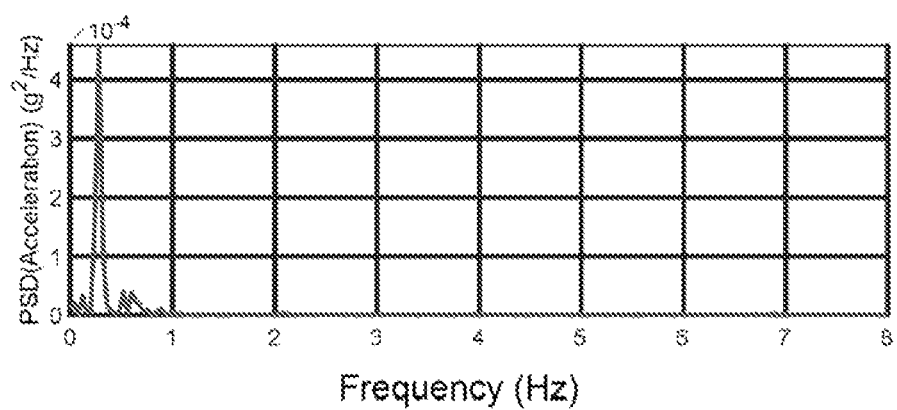
FIG. 6A shows the power spectral density of the acceleration signal of FIG. 4A.
Figure 6B:
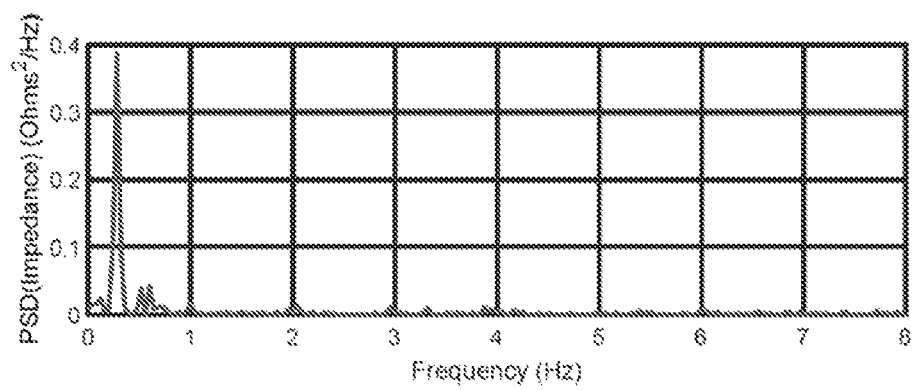
FIG. 6B shows the power spectral density of the impedance signal of FIG. 4B.

When looking at the power spectral densities (or shortly power spectra) of FIGS. 6A to 7B, the situation changes. Here, the power spectrum of the acceleration signal of the patient's natural respiration depicted in FIG. 6A and the power spectrum of the impedance signal of the patient's natural respiration depicted in FIG. 6B basically only contain signals having a frequency below 1 Hz. This threshold is valid both for the acceleration signal and the impedance signal, even though the bare signals are measured on a totally different scale. In this particular example, the relative power in the frequency band from 1 Hz to 8 Hz in FIG. 6A is only 9%.

Figure 7A:
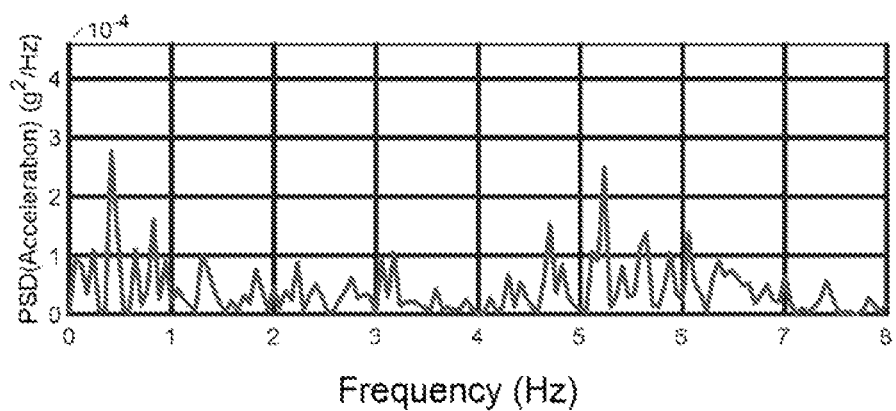
FIG. 7A shows the power spectral density of the acceleration signal of FIG. 5A.
Figure 7B:
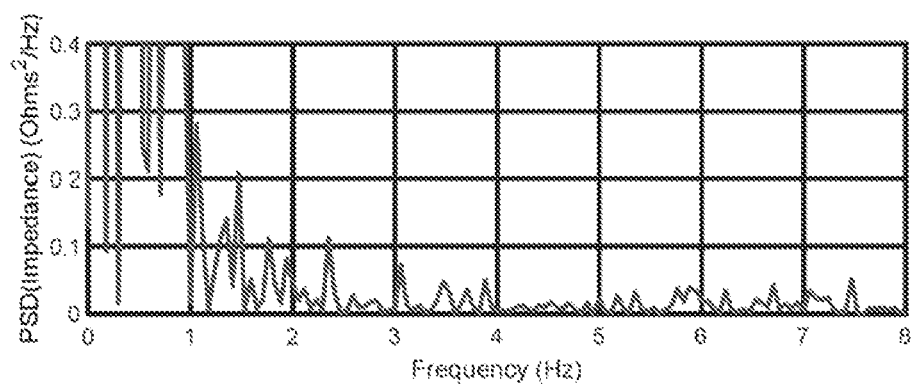
FIG. 7B shows the power spectral density of the impedance signal of FIG. 5B.

In contrast, the power spectrum of the acceleration data of the coughing patient (FIG. 7A) and the power spectrum of the impedance signal of the coughing patient (FIG. 7B) show a huge amount of signals having a frequency of more than 1 Hz, namely of between 1 Hz and 8 Hz. This high-frequency content in the power spectra of the acceleration data and the impedance data is used for identifying coughing of the patient and represents a much more reliable measure of such coughing than relying on the bare acceleration and impedance data depicted in FIGS. 5A to 5B. In this particular example, the relative power in the frequency band from 1 Hz to 8 Hz in FIG. 7A is 80%, well above the 60% threshold proposed to identify coughing, It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

LIST OF REFERENCE NUMBERS

10A—active medical device (wearable)
10B—active medical device (implantable)
20—heart
21—right ventricle
22—right atrium
30—human
40—evaluation unit
120—first processor
122—first memory unit
126—detection unit
130—first computer-readable program
132—accelerometer
420—second processor
422—second memory unit
430—second computer-readable program

What is claimed is:

1. An active medical device, comprising a processor, a memory unit, and a detection unit configured to detect a body impedance, wherein the memory unit comprises a computer-readable program that causes the processor to perform the following steps when executed on the processor:
    a) measuring a body impedance of a patient with the detection unit during a first period of time to obtain time-dependent impedance data and calculating a power spectral density of the impedance data (impedance PSD);
    b) identifying coughing of the patient when
        at least 1% of all values of the impedance PSD have a frequency of at least 1 Hz; and
        at least 60% of the power in the impedance PSD is contained in a frequency band of 1 to 8 HZ.

2. The active medical device according to claim 1, wherein the active medical device is a wearable device or an active implantable medical device.

3. The active medical device according to claim 1, wherein the active medical device is an implantable pulse generator, an implantable cardioverter-defibrillator, a cardiac resynchronization therapy device, or an implantable cardiac monitor.

4. The active medical device according to claim 1, wherein the detection unit is configured to detect a transthoracic body impedance.

5. The active medical device according to claim 1, wherein the computer-readable program causes the processor to additionally detect at least one of a position of the patient relative to a ground and an activity status of the patient with an accelerometer.

6. The active medical device according to claim 5, wherein the computer-readable program causes the processor to indicate a validity of the identification of coughing on the basis of at least one of the detected position and the detected activity status of the patient.

7. The active medical device according to claim 1, wherein the computer-readable program causes the processor to identify an amount of coughing events of the patient based on the identified coughing.

8. The active medical device according to claim 7, wherein the computer-readable program causes the processor to create an alert if the amount of coughing events of the patient exceeds a predetermined threshold.

9. An arrangement, comprising an active medical device and an evaluation unit separate from the active medical device, wherein the active medical device comprises a first processor, a first memory unit, and a detection unit configured to detect a body impedance, and a data communication unit, wherein the first memory unit comprises a first computer-readable program that causes the first processor to perform the following steps when executed on the first processor:
    a) measuring a body impedance of a patient with the detection unit during a first period of time to obtain time-dependent impedance data;
    b) transmitting impedance data obtained in step a) via the data communication unit to the evaluation unit located outside a body of the patient, wherein: the evaluation unit comprises a second processor and a second memory unit, wherein the second memory unit comprises a second computer-readable program that causes the second processor to perform the following steps when executed on the second processor:
    c) storing the transmitted impedance data in the second memory unit;
    d) calculating a power spectral density of the impedance data (impedance PSD);
    e) identifying coughing of the patient when:
        at least 1% of all values of the impedance PSD have a frequency of at least 1 Hz; and
        at least 60% of the power in the impedance PSD is contained in a frequency band of 1 to 8 Hz.

10. The arrangement according to claim 9, wherein the data communication unit is arranged and designed to transfer data to the evaluation unit via a wireless data communication.

11. The arrangement according to claim 10, wherein the wireless data communication is configured to use standard data transmission protocols or specifications.

12. A computer program product comprising non-transitory memory having computer-readable code stored thereon that causes a processor to perform the following steps when executed on the processor:
    a) measuring a body impedance of a patient with a detection unit of an active medical device during a first period of time to obtain time-dependent impedance data and calculating a power spectral density of the impedance data (impedance PSD);
    b) identifying coughing of the patient when:
        at least 1% of all values of the impedance PSD have a frequency of at least 1 Hz; and
        at least 60% of the power in the impedance PSD is contained in a frequency band of 1 to 8 Hz.

13. A method for automatically detecting coughing of a patient, the method comprising the following steps:
    a) measuring a body impedance of a patient with a detection unit of an active medical device during a first period of time to obtain time-dependent impedance data and calculating a power spectral density of the impedance data (impedance PSD);
    b) identifying coughing of the patient when:
        at least 1% of all values of the impedance PSD have a frequency of at least 1 Hz; and
        at least 60% of the power in the power impedance PSD is contained in a frequency band of 1 to 8 Hz.

14. The method according to claim 13, wherein the method further comprises indicating an increased risk of a COVID-19 infection if an amount of coughing events determined based on the identified coughing exceeds a predetermined threshold.

15. The method according to claim 13, wherein the method further comprises indicating an increased risk of an influenza infection if an amount of coughing events determined based on the identified coughing exceeds a predetermined threshold.

* * * * *